United States Patent
Durali et al.

(10) Patent No.: US 12,240,973 B2
(45) Date of Patent: Mar. 4, 2025

(54) ENDOLUMINAL DEVICE AND POLYMER

(71) Applicant: Endologix LLC, Irvine, CA (US)

(72) Inventors: Mehdi Durali, Irvine, CA (US); Lonnie Jones, Irvine, CA (US)

(73) Assignee: Endologix LLC, Irvine, CA (US)

( * ) Notice: Subject to any disclaimer, the term of this patent is extended or adjusted under 35 U.S.C. 154(b) by 818 days.

(21) Appl. No.: 16/756,800

(22) PCT Filed: Oct. 19, 2018

(86) PCT No.: PCT/US2018/056792
§ 371 (c)(1),
(2) Date: Apr. 16, 2020

(87) PCT Pub. No.: WO2019/083855
PCT Pub. Date: May 2, 2019

(65) Prior Publication Data
US 2020/0324018 A1    Oct. 15, 2020

Related U.S. Application Data

(60) Provisional application No. 62/575,827, filed on Oct. 23, 2017.

(51) Int. Cl.
*C08L 33/08* (2006.01)
*A61B 17/12* (2006.01)
(Continued)

(52) U.S. Cl.
CPC .......... *C08L 33/08* (2013.01); *A61L 24/0031* (2013.01); *A61L 24/06* (2013.01);
(Continued)

(58) Field of Classification Search
CPC .................. A61F 2/441; A61F 5/443; A61F 2013/00638; A61F 2013/00676; A61B 17/12181; A61L 24/0031
See application file for complete search history.

(56) References Cited

U.S. PATENT DOCUMENTS 4,068,027 A * 1/1978 Van Ornum .......... B29C 73/163
                                                                524/505
4,859,716 A * 8/1989 Ibsen .................. A61K 6/887
                                                                522/28

(Continued)

FOREIGN PATENT DOCUMENTS

| CN | 104558392 A | * | 4/2015 | |
| JP | 2009191260 A | * | 8/2009 | ............... C08F 2/44 |

OTHER PUBLICATIONS

Japanese Office Action dated Apr. 24, 2023, for application No. 2020-522283.
(Continued)

*Primary Examiner* — Michael C Romanowski
(74) *Attorney, Agent, or Firm* — Foley & Lardner LLP

(57) ABSTRACT

Various embodiments relate to compositions for use in endoluminal devices and to methods of using compositions in endoluminal devices. The compositions include two parts, a first part including a first solution and a second part including a second solution, wherein the first solution comprises one or more pre-polymers, a non-aqueous solvent, a polymerization co-initiator or initiator and optionally one or more chain extenders and additives, and the second solution comprises a polymerization initiator or co-initiator, a non-aqueous solvent and optionally one or more chain extenders and additives.

21 Claims, 6 Drawing Sheets

(51) Int. Cl.
 *A61F 2/07*  (2013.01)
 *A61L 24/00*  (2006.01)
 *A61L 24/06*  (2006.01)
 *C08F 220/28*  (2006.01)
 *C08F 222/10*  (2006.01)

(52) U.S. Cl.
 CPC ..... *C08F 222/103* (2020.02); *A61B 17/12113* (2013.01); *A61B 17/12195* (2013.01); *A61F 2/07* (2013.01); *A61L 2300/802* (2013.01); *A61L 2430/36* (2013.01); *C08F 220/286* (2020.02); *C08L 2205/025* (2013.01)

(56) References Cited

U.S. PATENT DOCUMENTS

| | | | | |
|---|---|---|---|---|
| 5,087,392 | A * | 2/1992 | Burke | G02B 1/043 |
| | | | | 264/2.6 |
| 5,739,176 | A | 4/1998 | Dunn et al. | |
| 6,586,246 | B1 * | 7/2003 | Yoon | A61L 27/18 |
| | | | | 435/395 |
| 6,818,018 | B1 | 11/2004 | Sawhney | |
| 7,193,007 | B2 * | 3/2007 | Cheng | A61L 27/16 |
| | | | | 524/916 |
| 11,180,627 | B2 * | 11/2021 | Hess | C09K 5/14 |
| 2008/0132587 | A1 * | 6/2008 | Montgomery | C08L 75/16 |
| | | | | 522/27 |
| 2010/0012263 | A1 | 1/2010 | Oshima et al. | |
| 2011/0092613 | A1 | 4/2011 | Khosravi et al. | |
| 2014/0273246 | A1 * | 9/2014 | Bisso | G07D 7/0043 |
| | | | | 436/56 |
| 2016/0324969 | A1 * | 11/2016 | Zook | A61K 47/32 |
| 2018/0112054 | A1 * | 4/2018 | Steiner, III | C08G 18/092 |
| 2019/0062517 | A1 * | 2/2019 | Steiner, III | C08J 9/28 |

OTHER PUBLICATIONS

International Search Report and Written Opinion dated Jan. 8, 2019, from application No. PCT/US2018/056792.

Extended European Search Report dated Jul. 20, 2021, from application No. 18870450.6.

International Preliminary Report on Patentability dated May 7, 2020, from application No. PCT/US2018/056792.

Japanese Office Action dated Jul. 29, 2022, from application No. 2020-522283.

European Office Action dated Jul. 5, 2024, for application No. 18870450.6.

* cited by examiner

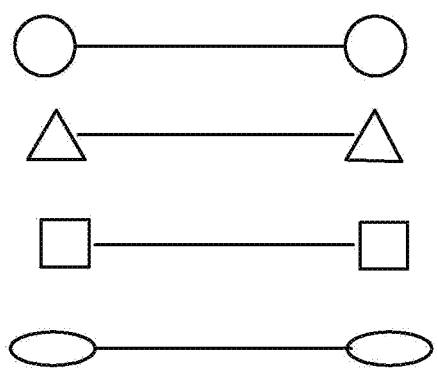
FIG. 5A
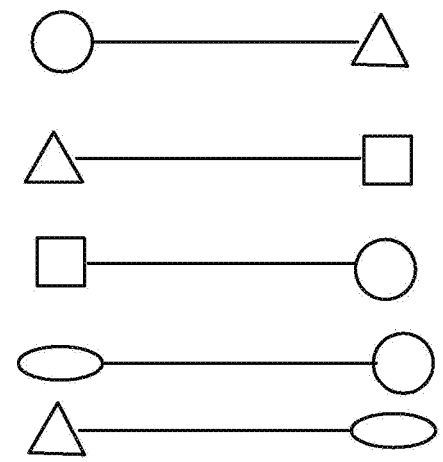
FIG. 5B
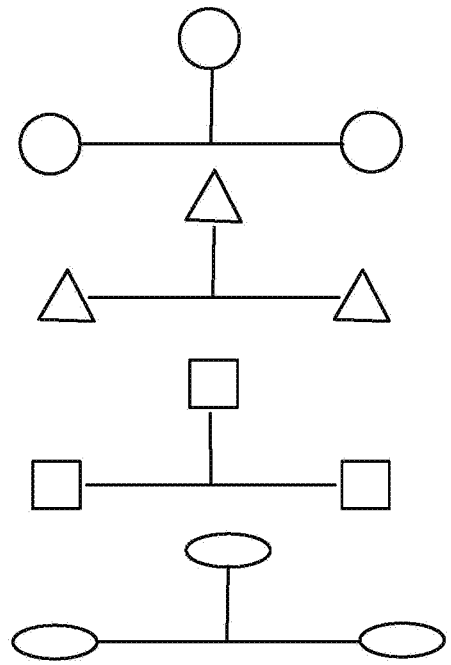
FIG. 5C
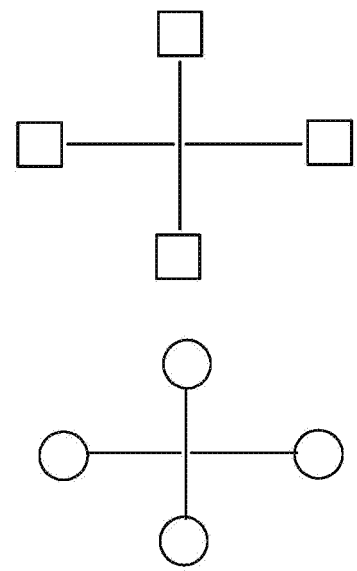
FIG. 5D
KEY:
○ Acrylate
△ Methacrylate
□ Vinyl
⬭ Allyl
FIG. 5E

ENDOLUMINAL DEVICE AND POLYMER

CROSS-REFERENCE TO RELATED PATENT APPLICATIONS

This application is a U.S. National Stage Application under 35 U.S.C. § 371 of International Application No. PCT/US2018/056792, filed Oct. 19, 2018, which claims priority from U.S. Provisional Application No. 62/575,827, filed Oct. 23, 2017, the entire contents of which are incorporated by reference herein.

FIELD

Embodiments disclosed herein relate generally to compositions for use in endoluminal devices and to methods of using compositions in endoluminal devices. Various embodiments relate to biostable organogels and methods for treating aneurysms.

BACKGROUND

Aneurysms are enlargements or bulges in blood vessels that are often prone to rupture and which therefore present a serious risk to a patient. Aneurysms may occur in any blood vessel but are of particular concern when they occur in the cerebral vasculature or the patient's aorta.

Abdominal aortic aneurysms (AAA's) are classified based on their location within the aorta as well as their shape and complexity. Aneurysms that are found below the renal arteries are referred to as infrarenal abdominal aortic aneurysms. Suprarenal abdominal aortic aneurysms occur above the renal arteries. Thoracic aortic aneurysms (TAA's) occur in the ascending, transverse, or descending part of the upper aorta. Infrarenal aneurysms are the most common, representing about 70% of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. A common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Endoluminal grafts have recently come into widespread use for the treatment of aortic aneurysms in patients. In general, endoluminal repairs access the aneurysm "endoluminally" through either or both common iliac arteries. The grafts are then implanted. Successful endoluminal procedures have a much shorter recovery period than open surgical procedures.

Typical endograft procedures utilize stent graft placement to treat an aneurysm. It would be desirable to provide improved compositions, methods, systems, and implanted prostheses which result in minimal or no leaks, resist migration, are relatively easy to position, and can treat most or all aneurismal configurations. Further it would be desirable to provide endoluminal graft filling structures and compositions which have suitable biocompatibility, biodegradability, viscosity, stability and balanced mechanical properties of flexibility and strength to endure the in vivo environment. At least some of these objectives will be met by the technology described hereinafter.

SUMMARY OF THE DISCLOSURE

Various embodiments relate to a composition comprising two parts, a first part including a first solution and a second part comprising a second solution, wherein the first solution comprises one or more pre-polymers, a non-aqueous solvent, a polymerization co-initiator or initiator and optionally one or more chain extenders and additives, and the second solution comprises a polymerization initiator or co-initiator, a non-aqueous solvent and optionally one or more chain extenders and additives. Various embodiments relate to an organogel comprising the composition.

In various embodiments, the pre-polymer comprises compounds having at least two functional groups selected from acrylate, methacrylate or vinyl functional groups.

In various embodiments, the pre-polymer is selected from the group consisting of ethoxylated (3) bisphenol A diacrylate, ethoxylated (30) bisphenol A diacrylate (EBPADA), ethoxylated (9) trimethylolpropane triacrylate, ethoxylated (15) trimethylolpropane triacrylate, ethoxylated (20) trimethylolpropane triacrylate (PEG-T), propoxylated (3) trimethylolpropane triacrylate (PTMPTA), pentaerythriol triacrylate, ethoxylated (4) pentaerythritol tetraacrylate, pentaerythritol tetraacrylate, and the methacrylic variants thereof, divinyl adipate, 1,4 dibutane diol divinyl ether, di and tri-ethylene glycol divinyl ether, allyl ether, diallyl maleate, trimethyl propane diallyl ether, and combinations thereof.

In various embodiments, the non-aqueous solvent comprises aliphatic and aromatic solvents selected from the groups consisting of alcohols, aldehydes, amides, carbonates, ethers, esters, glycols, glycol ethers, glycol esters, hydrocarbons, ketones, sulfoxides, and vegetable oils.

In various embodiments, the non-aqueous solvent is selected from the group consisting of methanol, glycerin, ethylene glycol, propylene glycol, butylene glycol, dipropylene glycol, diethylene glycol, tripropylene glycol, polyethylene glycol, ethyl ether, tripropylene glycol methyl ether, di(propylene glycol) butyl ether, propylene carbonate, butylene carbonate, benzene, toluene, xylene, methyl ethyl ketone, castor oil, linseed oil, sesame oil, soyabean oil, olive oil, and combinations thereof.

In various embodiments, the chain extender comprises mono- or di-functional compounds having acrylate, methacrylate or vinyl functional groups.

In various embodiments, the chain extender is selected from the group consisting of polyethylene glycol monoacrylate (PEGMA), polypropylene glycol monoacrylate (PPGMA), polyethylene glycol diacrylate (PEGDA), polypropylene glycol diacrylate (PPGDA), dipropylene glycol diacrylate (DPGDA), tetraethylene glycol diacrylate (TEGDA), tripropylene glycol diacrylate (TPGDA), polyethylene glycol mono methacrylate (PEGMMA), polypropylene glycol mono methacrylate (PPGMMA), polyethylene glycol methyl ether methacrylate (PEGMEMA), polyethylene glycol dimethacrylate (PEGDMA), polypropylene glycol dimethacrylate (PPGDMA), and combinations thereof.

In various embodiments, the polymerization initiator comprises peroxides and hydroperoxides.

In various embodiments, the polymerization initiator is selected from the group consisting of benzoyl peroxide (BPO), cumene hydroperoxide (CHP), Di-cumyl peroxide (CPO), lauryl peroxide, tert-amyl hydroperoxide (t-AHP), tert-butyl hydroperoxide (t-BHP), di-tert-butyl peroxide (DTBP), tributyl hydroperoxide (TBPH), tetra-methyl butyl hydroperoxide (MBHP), and combinations thereof.

In various embodiments, the polymerization co-initiator is selected from the group consisting of tri-ethanol amine (TEA), 1-(2-pyridyl)-2-thiourea (PTU), 1-acetyl-2-thiourea (ATU), N, N-dihydroxyethyl-p-toluidine (DHEPT), 4-(dimethyl amino) phenethyl alcohol (DMAPE), ethyl 4-(dimethylamino)benzoate (EDMAB), 2-[4-(dimethylamino)phenyl]ethanol, N,N-dimethyl-p-toluidine (DMPT), bis(hydroxyethyl)-p-toluidine, and combinations thereof.

In various embodiments, either or both of the first and second solutions further comprise a co-solvent.

In various embodiments, the co-solvent is selected from the group consisting of nonanol, dimethyl sulfoxide, butylene carbonate, di-ethylene glycol ethyl ether, di-propylene glycol methyl ether, di-propylene glycol butyl ether, tripropylene glycol methyl ether and tri-propylene glycol butyl ether, and combinations thereof.

In various embodiments, the composition further comprises one or more additives.

In various embodiments, the one or more additives are selected from the group consisting of fillers, contrast agents, processing aids, plasticizers, and viscosity-reducing agents.

Various embodiments relate to a method of forming an organogel including delivering a composition comprising a first solution and a second part comprising a second solution to the intended site of formation of the organogel; contacting the first solution with the second solution; and initiating polymerization of the pre-polymer to form an organogel; wherein the first solution comprises one or more pre-polymers, a non-aqueous solvent, a polymerization co-initiator or initiator and optionally one or more chain extenders and additives, and the second solution comprises a polymerization initiator or co-initiator, a non-aqueous solvent and optionally one or more chain extenders and additives.

In various embodiments, the one or more additives are selected from the group consisting of fillers, contrast agents, processing aids, plasticizers, and viscosity-reducing agents.

In various embodiments, the composition exhibits a compressive modulus of from about 1 MPa to about 18 MPa.

In various embodiments, the composition exhibits a gel time of about 1 min to about 20 min.

Various embodiments relate to a system for treating an aneurysm, where the system comprises a filling structure filled with a composition comprising two parts, a first part including a first solution and a second part comprising a second solution, wherein the first solution comprises one or more pre-polymers, a non-aqueous solvent, a polymerization co-initiator or initiator and optionally one or more chain extenders and additives, and the second solution comprises a polymerization initiator or co-initiator, a non-aqueous solvent and optionally one or more chain extenders and additives.

BRIEF DESCRIPTION OF THE DRAWINGS

FIGS. 5A, 5B, 5C, and 5D illustrate pre-polymer having various functional groups, in accordance with embodiments of the present technology.

FIG. 5E provides a key for the shapes in FIGS. 5A, 5B, 5C, and 5D.

DETAILED DESCRIPTION

Figure 1:
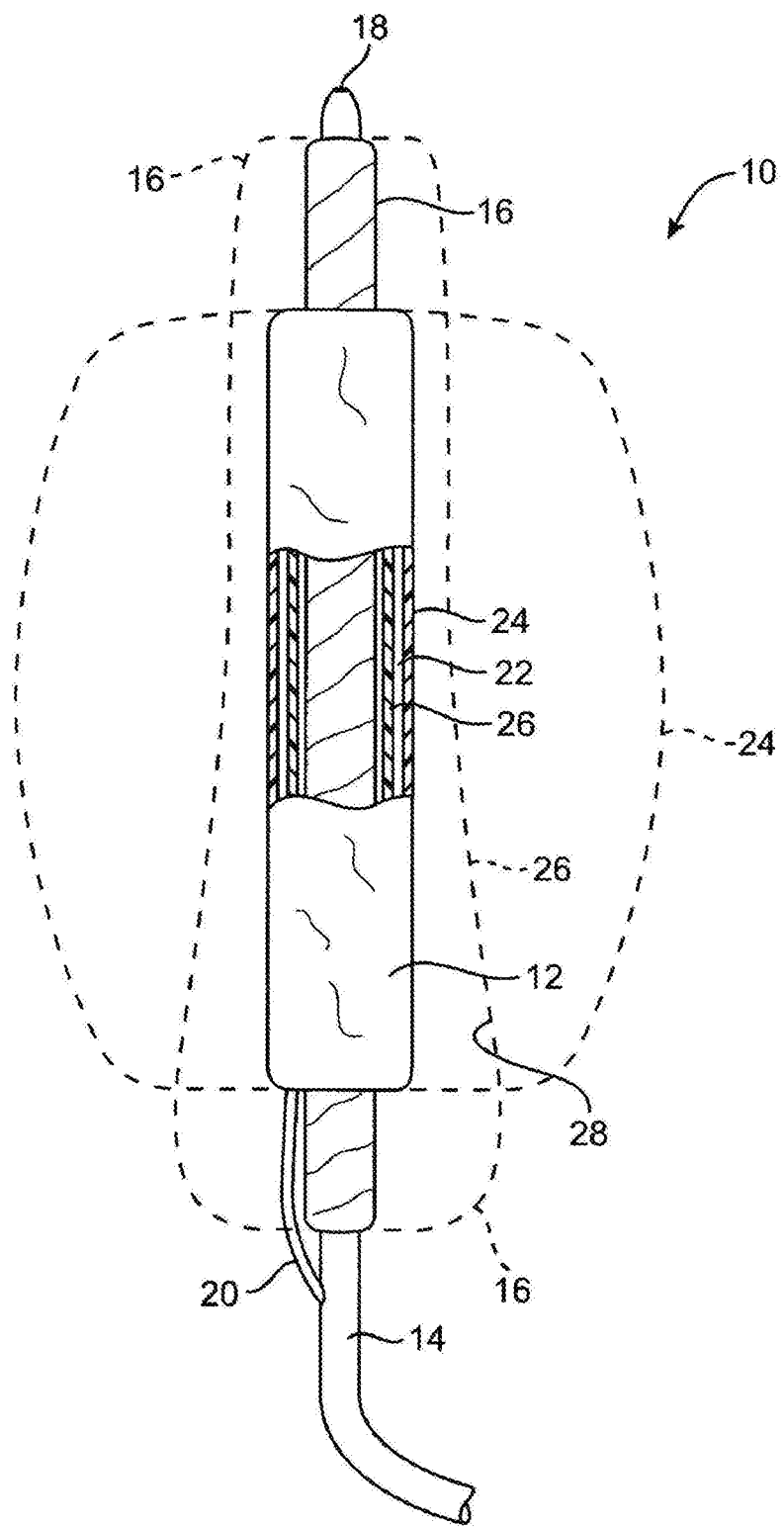
FIG. 1 illustrates a prosthesis system comprising a filling structure mounted over a delivery catheter, and fillable with a composition of the present technology.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and may be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "and/or" includes any and all combinations of one or more of the associated listed items.

Ratio, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, 5 to 40 mole % should be interpreted to include not only the explicitly recited limits of 5 to 40 mole %, but also to include sub-ranges, such as 10 mole % to 30 mole %, 7 mole % to 25 mole %, and so forth, as well as individual amounts, including fractional amounts, within the specified ranges, such as 15.5 mole %, 29.1 mole %, and 12.9 mole %, for example.

As used herein, the term "organogel" refers to a class of gel composed of a liquid organic phase within a three-dimensional, cross-linked network.

As used herein, the term "initiator" refers to an element which begins the process of gelation of a curable composition. In some cases, the term "initiator" as used herein refers to one part of an initiator system. For example, a two part initiator system may be used wherein one part is included in the curable composition and the other part is separately provided. The separately provided other part is referred to as the "co-initiator" herein.

"Substantially free from water," as used herein, means that the water content in the composition is less than about 1% of the total weight of the composition. By "substantially non-aqueous" or having "low water content" it is meant that the amount of water if present in the composition is small and is less than about 1.0%, preferably less than about 0.5% and more preferably less than about 0.2%. For example, the compositions described herein may be substantially free of water or substantially non-aqueous or have low water content. While water is not an intended ingredient of the compositions, it might exist in small quantities as an impurity. However, typically, the compositions described herein are free from water.

Methods which use an endobag or fillable structure for treating AAA generally include forming a material in-situ by increasing the volume of an expandable member of a medical device. The expandable member is typically filled with a filling material such as Polyethylene Glycol (PEG) or another polymer that may be polymerized in situ in presence of water to form a hydrogel. The hydrogel material conforms to the shape of the aneurysm being treated, and also helps to secure of the medical device in place. The material is formed by the polymerization of polymer precursors (pre-polymers) mixed with one or more of crosslinking agent and a free radical initiator and/or co-initiator. The polymerization may be conducted, for example, inside an endograft comprising a single-walled or double-walled bag, such as an endobag. It has now been found that organogel materials having superior stability and desired mechanical properties can be prepared and be employed as filling materials for an expandable member of a medical device.

In various embodiments, the present technology provides biocompatible organogels for therapeutic applications, such as treatment of abdominal and thoracic aortic aneurysms. The organogel is formed from a curable composition which includes one or more gellable pre-polymers that can be cured or modified, in situ, at the intended site of application, in response to an initiator system, and which is configured to undergo a change in its physical state in order to retain a desired configuration and position. The curable composition, formed from the pre-polymers, and optionally other components, is deliverable to the intended site of application. The properties of the curable composition, e.g., viscosity, will vary depending upon the intended final use of the composition. The composition is delivered to the intended site through an appropriate delivery device, such as a catheter or syringe. Before, during, or after delivery, the composition is exposed to the initiator system, causing the composition to undergo one or more of curing, crosslinking and gelation to provide the organogel containing device.

In one aspect, provided is a composition, including two parts, wherein at least one of the parts includes a pre-polymer in a non-aqueous solvent which forms an organogel when the two parts are combined. The composition includes a pre-polymer which can rapidly crosslink after delivery to the intended site, to form an organogel. The composition further includes one or more non-aqueous solvents, polymerization aids such as redox components, and may include additives and active agents. The composition is suitable for forming an organogel in situ, at the intended site of application. Typically, all components contributing to the formation of organogel are soluble in the non-aqueous solvent.

In various embodiments, provided is a composition, including two parts, the first part including a first solution and a second part including a second solution. In various embodiments, the compositions include two parts, a first part including a first solution and a second part including a second solution, wherein the first solution comprises one or more pre-polymers, a non-aqueous solvent, a polymerization co-initiator or initiator, and optionally one or more chain extenders and additives, and the second solution comprises a polymerization initiator or co-initiator, a non-aqueous solvent and optionally one or more chain extenders and additives. Although various embodiments are generally described in terms of two solutions, the present technology may include a composition comprising a first part including a solution and a second part including a solid (e.g., powder), or both parts including solids rather than solutions of the respective components.

The pre-polymers may include multifunctional crosslinking pre-polymers. The multifunctional pre-polymer may either include similar functional groups or different functional groups. In various embodiments, the pre-polymers include compounds which include at least one functional group selected from acrylate, methacrylate, vinyl or allyl functional groups. In various embodiments, the compound comprising at least one functional group may react with another compound containing a functional group selected from acrylate, methacrylate, vinyl or allyl functional groups to form a covalent bond. In various embodiments, the pre-polymers include compounds which include at least two functional groups selected from acrylate, methacrylate, vinyl or allyl functional groups. In at least one embodiment, suitable pre-polymers include, but are not limited to, polyethylene glycol based acrylate, methacrylate, vinyl and allyl compounds. Some examples of such compounds include PEG acrylates and methacrylates selected from ethoxylated (3) bisphenol A diacrylate, ethoxylated (30) bisphenol A diacrylate (EBPADA), ethoxylated (9) trimethylolpropane triacrylate, ethoxylated (15) trimethylolpropane triacrylate, ethoxylated (20) trimethylolpropane triacrylate (PEG-T), propoxylated (3) trimethylolpropane triacrylate (PTMPTA), pentaerythritol triacrylate, pentaerythritol tetraacrylate, ethoxylated (4) pentaerythritol tetraacrylate, and the methacrylic variants thereof, and vinyl and allyl compounds selected from, divinyl adipate, 1,4 dibutane diol divinyl ether, di and tri-ethylene glycol divinyl ether, allyl ether, diallyl maleate, trimethyl propane diallyl ether, and the like and mixtures thereof. In an illustrative embodiment, the pre-polymer includes ethoxylated (20) trimethylolpropane triacrylate. In at least one embodiment, the pre-polymers have an average molecular weight ranging from 100 to 8000. Exemplary pre-polymer having various functional groups are illustrated in FIGS. 5A, 5B, 5C, and 5D. FIG. 5E provides a key for the shapes in FIGS. 5A, 5B, 5C, and 5D. While the exemplary compositions of the dimers, trimers, and tetramers depicted in some of the figures have the same functional groups, the functional groups on the dimers, trimers, and tetramers could be all the same type or a combination of any of the various functional groups disclosed herein.

The pre-polymer may be added in a suitable amount to obtain an organogel with the desired properties. The pre-polymer may be present in an amount of about 1% to about 80% by weight of the total weight of the composition. This may include from about 5% to about 75%, about 10% to about 70%, about 15% to about 65%, about 20% to about 60%, about 25% to about 55%, about 30% to about 50%, or about 35% to about 45%, by weight of the total weight of the composition, and ranges between and including any two of these values, or less than any one of these values. In an illustrative embodiment, the pre-polymer is present in an amount of from about 10% to about 40% by weight of the total weight of the composition.

The first solution and optionally the second solution may or may not include a non-aqueous solvent. The non-aqueous solvent may be such that it dissolves the pre-polymer and other components, while being inert to all reactants. Suitable non-aqueous solvents include, but are not limited to, aliphatic and aromatic solvents, including, but not limited to, alcohols, aldehydes, amides, carbonates, ethers, esters, glycols, glycol ethers, glycol esters, hydrocarbons, ketones, and sulfoxides, vegetable oils and fats and the like and combinations thereof, and other non-aqueous solvents known to those skilled in the art. Illustrative solvents include, but are not limited to methanol, glycerin, ethylene glycol, propylene glycol, butylene glycol, dipropylene glycol, diethylene glycol, tripropylene glycol, polyethylene glycol, ethyl ether, tripropylene glycol methyl ether, di(propylene glycol) butyl ether, propylene carbonate, butylene carbonate, benzene, toluene, xylene, methyl ethyl ketone, dimethyl sulfoxide, castor oil, linseed oil, sesame oil, soybean oil, olive oil, and the like, and mixtures thereof.

The non-aqueous solvent may be present in the composition in an amount from about 1 wt. % to about 90 wt. %. This may include from about 5% to about 80%, about 10% to about 70%, about 15% to about 65%, about 20% to about 60%, about 25% to about 55%, about 30% to about 50%, or about 35% to about 45%, by weight of a non-aqueous solvent of the total weight of the composition. In various embodiments, the first and the second solution may include about 1 wt. %, about 5 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, about 75 wt. %, about 80 wt. %, about 85 wt %, about 90 wt. %, of non-aqueous solvent and ranges between and including any two of these values, or less than any one of these values. In an illustrative embodiment, the first solution includes from about 20 wt. % to about 80 wt. % of one or more non-aqueous solvents. In an illustrative embodiment, the second solution includes from about 20 wt. % to about 80 wt. % of one or more non-aqueous solvents. In an illustrative embodiment, the non-aqueous solvent is present in an amount of from about 10% to about 40% by weight of the total weight of the composition.

In addition to the pre-polymer and the solvent, the composition may optionally include one or more chain extenders. The properties of the organogel can be modified by appropriate selection of the chain extenders. For example, chain extenders may be utilized to break into the tight crosslinked networks of the organogel and increase toughness. Suitable chain extenders are those which are soluble in the non-aqueous solvent and are capable of undergoing polymerization with the prepolymer or forming an independent network within the organogel structure. The chain extender may include a di-functional extending monomer and/or a mono-functional extending monomer. In various embodiments, suitable chain extenders include any mono or di-functional acrylate, methacrylate, vinyl or allyl compound. Examples of such suitable chain extenders include, but are not limited to, polyethylene glycol monoacrylate (PEGMA), polypropylene glycol monoacrylate (PPGMA), polyethylene glycol diacrylate (PEGDA), polypropylene glycol diacrylate (PPGDA), dipropylene glycol diacrylate (DPGDA), tetraethylene glycol diacrylate(TEGDA), tripropylene glycol diacrylate (TPGDA), polyethylene glycol mono methacrylate (PEGMMA), polypropylene glycol mono methacrylate (PPGMMA), polyethylene glycol methyl ether methacrylate (PEGMEMA), polyethylene glycol dimethacrylate (PEGDMA), polypropylene glycol dimethacrylate (PPGDMA), and the like and mixtures thereof.

The chain extender may suitably have a number average molecular weight (Mn) in the range of about 200 to about 25,000 Daltons. This includes, a number average molecular weight of about 200 Daltons, about 400 Daltons, about 600 Daltons, about 800 Daltons, about 1,000 Daltons, about 2,000 Daltons, about 3,000 Daltons, about 4,000 Daltons, about 5,000 Daltons, about 6,000 Daltons, about 7,000 Daltons, about 8,000 Daltons, about 9,000 Daltons, about 10,000 Daltons, about 11,000, Daltons, about 12,000 Daltons, about 13,000 Daltons, about 14,000 Daltons, about 15,000 Daltons, about 20,000 Daltons, about 25,000 Daltons, and values between and including any two of these values, or less than any one of these values. In at least one embodiment, the chain extender may have a number average molecular weight of about 200 to about 15,000 Daltons. In at least one embodiment, the chain extender may have a number average molecular weight in the range of about 200 to about 10,000 Daltons. In at least one embodiment, the chain extender may have a number average molecular weight in the range of about 200 to about 2000 Daltons. Accordingly, illustrative chain extenders include, but are not limited to, PEGMMA 500, PEGMEMA 950, PEGDA 500, PEGDA 1000, PEGDA 2000, PEGDMA 300, PEGDMA 700, PEGDMA 1000, PEGDMA 2000, PPGDMA 1000, PPGDMA 2000, PEGDMA 10,000 and the like, and mixtures thereof.

In at least one embodiment, the chain extender is present in the composition at a concentration from about 0 wt. % to about 70 wt. %. This may include from about 1% to about 60%, about 5% to about 50%, about 10% to about 40%, about 15% to about 30%, about 20% to about 25%, by weight of a chain extender, of the total weight of the composition. In various embodiments, the first and/or the second solution may include one or more chain extender in an amount of 0 wt. %, about 1 wt. %, about 2 wt. %, about 5 wt. %, about 8 wt. %, about 10 wt. %, about 12 wt. %, about 15 wt. %, about 18 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, and ranges between and including any two of these values, or less than any one of these values. In an illustrative embodiment, the first solution includes from about 0 wt. % to about 40 wt. % of the chain extender, of the total weight of the composition. In other embodiments, the first solution includes from about 5 wt. % to about 30 wt. % of the chain extender, of the total weight of the composition.

Gelation and crosslinking of the pre-polymers can occur by a number of mechanisms, such as chemical or physical crosslinking, including, but not limited to, free radical polymerization, condensation polymerization, complexation, hydrogen bonding, and the like. In various embodiments, the organogel may further include an initiator/co-initiator pair to facilitate free-radical polymerization of the pre-polymer at physiological temperature. The initiator and co-initiator are included in separate solutions of the two-part composition. The initiator may include peroxides, hydroperoxides and any other peroxides containing compound. Suitable polymerization initiators include, but are not limited to, benzoyl peroxide (BPO), cumene hydroperoxide (CHP), Di-cumyl peroxide (CPO), lauryl peroxide, tert-amyl hydroperoxide (t-AHP), tert-butyl hydroperoxide (t-BHP), di-tert-butyl peroxide (DTBP), tributyl hydroperoxide (TBPH), tetra-methyl butyl hydroperoxide (MBHP), and the like, and mixtures thereof.

The compositions also include a co-initiator, which, when combined with the initiator brings about the curing of the pre-polymer at physiological temperature. In at least one embodiment, the co-initiator may be a secondary or tertiary amine. Suitable co-initiators include, but are not limited to, N,N di-methyl aniline, tri-ethanol amine (TEA), 1-(2-pyridyl)-2-thiourea (PTU), 1-acetyl-2-thiourea (ATU), N, N-dihydroxyethyl-p-toluidine (DHEPT), 4-(di-methyl amino) phenethyl alcohol (DMAPE), ethyl 4-(dimethylamino)benzoate (EDMAB), 2-[4-(dimethylamino)phenyl] ethanol, N,N-dimethyl-p-toluidine (DMPT), bis(hydroxyethyl)-p-toluidine, and the like, and mixtures thereof.

The amount of polymerization initiator and co-initiator can be varied depending upon the desired level of cross-linking and polymerization rate. Examples of the amount of one or more polymerization initiator and of one or more co-initiator in total wt. % of the composition include about 0.005 wt. %, about 0.001 wt. %, about 0.01 wt. %, about 0.05 wt. %, about 0.1 wt. %, about 0.2 wt. %, about 0.5 wt. %, about 1 wt. %, about 2 wt. %, about 3 wt. %, about 4 wt. %, about 5 wt. %, about 6 wt. %, about 7 wt. %, about 8 wt. %, about 10 wt. %, about 15 wt. %, about 20 wt. %, about 25 wt. %, about 30 wt. %, and ranges between and including any two of these values, or less than any one of these values. In at least one embodiment, the first solution includes from about 0.01 wt. % to about 3 wt. % of the initiator. In other embodiments, the second solution includes from about 0.01 wt. % to about 3 wt. % of the co-initiator.

In an illustrative embodiment, the first solution includes from about 0.5 wt. % to 1.5 wt. % of cumene hydroperoxide. In another illustrative embodiment, the second solution includes from about 0.5 wt. % to 1.5 wt. % of 1-(2-pyridyl)-2-thiourea.

In at least one embodiment, a composition of the present technology may also include a polymerization inhibitor, which may be included in one or both of the solutions of the two-part organogel formulation. The role of inhibitor is to prevent premature polymerization of prepolymers and chain extenders. The inhibitor action may not be permanent and in exemplary embodiments the inhibitor insures the stability of the composition in storage. Upon combination of the two components of the formulation, polymerization reaction is initiated, which leads to the formation of an organogel. Examples of suitable polymerization inhibitors include, but are not limited to, hydroquinone (HQ), methyl ether hydroquinone (MEHQ), butylated hydroxyl toluene (BHT), 4-tert-butylpyrocatechol, tert-butylhydroquinone, 1,4-benzoquinone, 6-tert-butyl-2,4-xylenol, 2,6-Di-tert-butylphenol, 1,1-Diphenyl-2-picrylhydrazyl, phenothiazine and the like.

The inhibitor may be present in the formulation in an amount of less than 3 wt. % on reactive components, less than about 1 wt. % or less than about 0.1 wt. %.

A composition of the present technology may further include one or more additive to modify or improve properties such as density, viscosity, dispensability, mechanical properties or visual characteristics such as to aid illumination under scans, or the like. In various embodiments the compositions may include one or more additives such as fillers, contrast agents, processing aids, plasticizers, viscosity-reducing agents, high molecular weight polymers, bulking agents, stabilizers, microspheres, fibers, powders, gasses, radiopaque materials, drugs, and the like. Exemplary additives include dimethyl 3,3'-thiodipropionate, sodium diatrizoate, butylene carbonate, polyurethanes, collagen, polyethylene glycols, microspheres, and the like. In at least one embodiment, the one or more additives may be included in the first solution or the second solution, or both solutions. In at least one embodiment, the first solution further includes one or more additives. In at least one embodiment, the second solution further includes one or more additives. In at least one embodiment, the one or more additives are selected from the group consisting of fillers, contrast agents, processing aids, plasticizers, and viscosity-reducing agents.

In at least one embodiment, a composition of the present technology may further include an effective amount of one or more pharmacologically active agents suitable for administration which would induce a desired systemic or local effect. Suitable pharmacologically active agents will be apparent to those skilled in the art and include, but are not limited to enzymes, proteins, anti-inflammatory agents, antibiotics, antiseptics, antineoplastic agents, cytotoxins, antifungal agents, antiviral agents, analgesics, growth factors, vasodilators, anesthetic agents, and the like or combinations thereof.

The viscosity of the first and/or the second solutions of the two-part composition may optionally be modified using viscosity-adjusting agents, emulsifiers, or miscible co-solvents, so as to permit ease of dispensing of the organogel. Suitable viscosity-adjusting co-solvents include aliphatic and aromatic solvents including hydrocarbons, alcohols, aldehydes, amides, carbonates, ethers, esters, glycols, glycol ethers, glycol esters, ketones, sulfoxides and other non-aqueous solvents known to the skilled in the art. Examples of such solvents include, but are not limited to, nonanol, dimethyl sulfoxide, butylene carbonate, di-ethylene glycol ethyl ether, di-propylene glycol methyl ether, di-propylene glycol butyl ether, tri-propylene glycol methyl ether and tri-propylene glycol butyl ether, and the like, or combinations thereof. In an illustrative embodiment, the composition includes nonanol as a co-solvent.

The compositions may include a biocompatible contrast agent or other additives to effect visualization in vivo and allow the device to be imaged for delivery, tracking, positioning, and other purposes. Where the composition includes a contrast agent, illustrative contrast agents include, but are not limited to ionic and nonionic agents such as iocarmic acid, iodipamide, iodoxamic acid, ioxaglic acid, acetrizoic acid, diatrizoic acid, iodamic acid, ioglicic acid, iopanoic acid, iopronic acid, iothalamic acid, ioxitalamic acid, ipodic acid, metrizoic acid, and their pharmaceutically acceptable salts, iodixanol, ioforminol, iotrolan, iobitridol, iohexol, iomeprol, iopamidol, iopentol, iopromide, iosimide, ioversol, ioxilan, and metrizamide and the like and combinations thereof. In at least one embodiment, the contrast agent includes sodium diatrizoate hydrate (NaDi), sodium amidotrizoate, sodium tyropanoate, sodium phentetiothalein, sodium calciumedetate, meglumine amidotrizoate, meglumine diatrizoate, triphenyl bismuth, zirconium oxide, aluminum oxide, barium sulfate, metrizamide, metrizoic acid, phenobutiodil, Iodixanol, and the like, or combinations thereof.

The compositions may further include viscosity reducing agent in an amount sufficient to reduce the viscosity of the polymeric composition while maintaining suitable flowability to facilitate its delivery to the intended site of application. Suitable viscosity reducing agents, include, but are not limited to polyethylene glycol polymers, hydrophilic, hydrophobic or amphiphilic surfactants, organic solvents, and the like or combinations thereof.

In various embodiments, additives and pharmacologically active agents, if present, can be incorporated in the composition at a concentration in the range of about 0.001 wt. %, about 0.01 wt. %, about 0.02 wt. %, about 0.05 wt. %, about 0.1 wt. %, about 0.5 wt. %, about 1.0 wt. %, about 2 wt. %, about 5 wt. %, about 10.0 wt. %, about 15.0 wt. %, about 20.0 wt. %, and ranges between any two of these values or less than any one of these values. For example, the composition may include from about from about 0.1 wt. % to 10.0 wt. % of a contrast agent.

In one aspect, provided is a composition, including two parts, wherein the first part includes a multifunctional crosslinking pre-polymer and a di-functional chain extender, a tertiary amine co-initiator, a non-aqueous solvent, and optionally a co-solvent; and the second part includes a peroxide initiator, a non-aqueous solvent, and optionally a co-solvent. Suitable multifunctional crosslinking pre-polymer, di-functional chain extenders, peroxide initiators, amine co-initiators, and non-aqueous solvents and co-solvents are as described herein. In at least one embodiment, the multifunctional crosslinking pre-polymer includes ethoxylated trimethylolpropane triacrylate. In at least one embodiment, the di-functional chain extender is selected from the group consisting of polyethylene glycol mono methacrylate, polyethylene glycol dimethacrylate, polyethylene glycol methylether methacrylate, polypropylene glycol diacrylate and polypropylene glycol dimethacrylate. In at least one embodiment, the non-aqueous solvent is selected from the group consisting of, propylene glycol, dipropylene glycol, tripropylene glycol, tripropylene glycol methyl ether, di(ethylene glycol) ethyl ether, di(propylene glycol) butyl ether, butylene carbonate, and combinations thereof. In at least one embodiment, the co-solvent includes nonanol. In at least one embodiment, the peroxide initiator is selected from cumene hydroperoxide and benzoyl peroxide. In at least one embodiment, the tertiary amine co-initiator is selected from the group consisting of 1-(2-pyridyl)-2-thiourea, N, N-dihydroxyethyl-p-toluidine, and 1-acetyl-2-thiourea. In at least one embodiment, the composition includes a first solution which includes ethoxylated (20) trimethylolpropane triacrylate, polyethylene glycol dimethacrylate, 1-(2-pyridyl)-2-thiourea and propylene glycol, and a second solution which includes, cumene hydroperoxide and propylene glycol. In at least one embodiment, the first solution and/or the second solution further includes a contrast agent. In at least one embodiment, the contrast agent is sodium diatrizoate hydrate.

In various embodiments, an organogel prepared using the compositions described herein is provided. In exemplary embodiments, provided is an organogel including a composition which includes two parts, a first part comprising a first solution and a second part comprising a second solution, wherein the first solution comprises a pre-polymer, a non-aqueous solvent, a polymerization co-initiator and optionally a chain extender; and the second solution comprises a polymerization initiator and a non-aqueous solvent. In various embodiments, an organogel including a crosslinkable or curable pre-polymer selected from ethoxylated (9) trimethylolpropane triacrylate, ethoxylated (15) trimethylolpropane triacrylate, ethoxylated (20) trimethylolpropane triacrylate (PEG-T), and propoxylated (3) trimethylolpropane triacrylate (PTMPTA), with a redox initiator and co-initiator pair, in a non-aqueous solvent is provided. The organogel does not swell or shrink substantially and the weight of the swollen organogel remains unchanged over time.

In various embodiments, an organogel prepared using the methods described herein is provided. In at least one embodiment, the method includes delivering a composition including a first part including a first solution and a second part including a second solution to the intended site of formation of the organogel; contacting the first solution with the second solution; and initiating polymerization of the pre-polymer to form an organogel. The first and the second solution are as described herein. In various embodiments, the first solution includes a pre-polymer, a non-aqueous solvent, a polymerization co-initiator and optionally a chain extender, and the second solution includes a polymerization initiator and a non-aqueous solvent.

In another aspect, provided is a method for providing a system, wherein the system includes a filling structure fillable with a composition which is adapted to be polymerized to form a matrix suitable for in vivo application. The method includes delivering a filling structure fillable with a composition comprising the two-part composition described herein and initiating polymerization of the pre-polymer in vivo to form an organogel. Suitable delivery protocols used for delivering the compositions may include, but are not limited to, delivery catheters having a balloon or other expandable support for carrying the filling structure. In various embodiments, the method includes filling a filling structure with the two-part composition described herein and initiating polymerization of the pre-polymer in vivo to form an organogel. In various embodiments, the filling structure is filled through a fill line.

The polymerization may be initiated by methods such as, but not limited to, free-radical initiation, thermal initiation, or by exposure to visible light. In at least one embodiment, the polymerization may be initiated using redox radically initiated solution polymerization. Thus, in at least one embodiment, the polymerization and crosslinking is initiated by using a polymerization initiator and co-initiator system. Suitable pre-polymers, chain extenders, solvents, initiators and co-initiators are as described herein.

The organogel may be formed by injecting the two-part composition into an implantable device where it undergoes cure resulting in a durable and biostable organogel. In one aspect, a method of forming an organogel in situ is provided. The method includes delivering an implantable device comprising a two-part composition to the intended site of formation of the organogel. The composition may be delivered as liquids, gels, foams, slurries, or the like. The composition includes pre-polymers described herein, which, after curing, will have a fixed shape. In at least one embodiment, the filling material may include two-part composition systems as described herein. In other embodiments, the filling material may include a single composition which, when exposed to the physiological environment, cures or hardens over time. Methods for curing or hardening the filling material will depend on the nature of the filling material. For example, certain pre-polymers may be cured by the application of energy, such as ultrasonic energy or visible light. Other pre-polymers may be cured when exposed to body temperature, or other conditions which cause polymerization of the composition. Still other compositions are such that the components may be mixed immediately prior to use and cured after a fixed time.

In various embodiments, each part of the composition will be fluid initially to permit delivery to the intended site and will be curable or otherwise hardenable so that, once in place, the composition, and the filling structure it is filled into or incorporated into, will remain in position after the delivery system is removed. An aspect of the present technology provides a composition for endoluminal applications, which can be easily delivered and which has stable properties.

Figure 6:
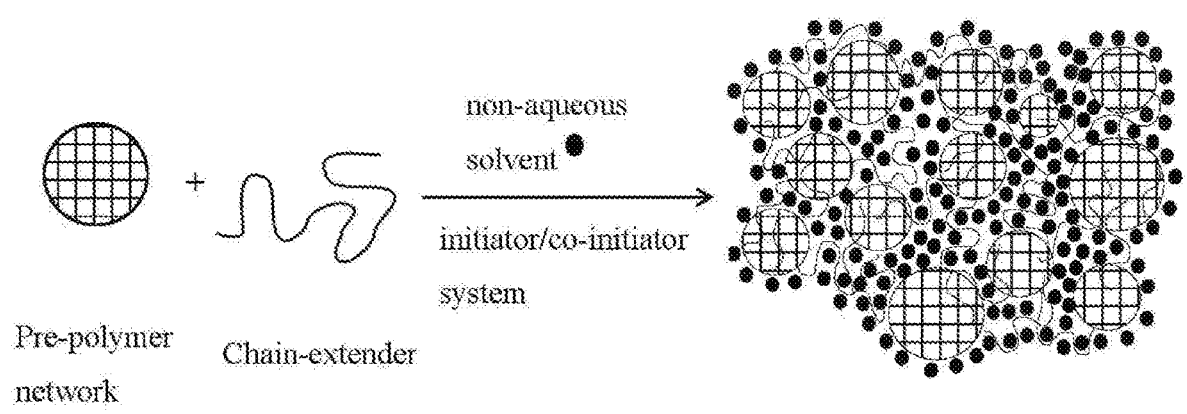
FIG. 6 illustrates formation of organogel composition, in accordance with an embodiment of the present technology.

In various embodiments, the compositions provide improved properties, including an improved combination of such properties as compressive strength, hardness, cure characteristics, acceptable reaction exotherm, ease of sterilization, room temperature storage stability, biocompatibility, in-service durability, and low shrinkage-swelling, as compared to compositions previously known. The improvement can be achieved without detrimental effect on other desired properties, including those that arise prior to or during delivery, during or following curing and in the course of extended use in vivo. Properties of the final organogel may be varied, for example by selecting appropriate specific gravities and viscosities of the first and second part of the two-part composition. The properties of the first solution and/or the second solution can be varied to provide organogels having the desired characteristics for the application. For example, the first and/or the second solution may have a high specific gravity and low viscosity for ease of delivery to the intended site of application. Various embodiments relate to an organogel comprising the composition. In an exemplary embodiment, provided herein is an organogel comprising a super network comprising pre-polymer networks comprising pre-polymers described herein, the networks being covalently bonded by chain extenders, e.g. as shown in FIG. 6.

The organogel may have a viscosity of about 100 cP or less, including, but not limited to, about 80 cP or less, about 50 cP or less, for example, about 45 cP or less, about 40 cP or less, about 35 cP or less, about 30 cP or less, about 25 cP or less, about 20 cP or less, or about 10 cP or less. In at least one embodiment, viscosity of the organogel is about 5 cP to about 50 cP, for example about 10 cP to about 30 cP, about 15 cP to about 25 cP; the viscosity is measured in Centipoise (cP), at 25° C., 30% solution.

The organogel may have a specific gravity in the range from about 0.1 to about 5, including, but not limited to, from, about 0.2 to 2, about 0.3 to 1.8, about 0.5 to 1.5, or about 0.8 to 1.3. In at least one embodiment, the organogel has a specific gravity of about 0.85 to about 1.25. In at least one embodiment, the organogel has a specific gravity which is generally the same as blood or thrombus.

The organogel may have a shore hardness in the range from about 1 durometer to about 400 durometer, including, but not limited to, about 2 durometer to about 300 durometer, about 5 durometer to about 200 durometer, about 10 durometer to about 140 durometer, or about 50 durometer to about 100 durometer.

Once the first and second solutions of the two-part composition are mixed together, the curing may occur rapidly, but through various stages where the composition goes from liquid to plastic or elastomeric to an organogel consistency. The organogel composition is an injectable solution and the clinically relevant time is the working time which is defined as the time period during which the solution can be injected or pumped through a narrow tube. The time required during which the gel cures and attains its full mechanical properties is the total cure time.

Accordingly, in at least one embodiment, the organogel has a gel set time of about 30 s to about 30 min. This includes a gel set time of about 30 s to about 20 min, about 45 s to about 15 min, about 1 min to about 10 min, and ranges between and including any two of these values, or less than any one of these values.

In at least one embodiment, the organogel has a cure time of less than about 25 min. This includes a cure time of less than about 20 minutes, less than about 15 min or less than about 10 min. In at least one embodiment, the organogel has a cure time of from about 30 s to about 10 min, about 1 min to about 8 min, about 3 min to about 5 min, and ranges between and including any two of these values, or less than any one of these values.

The organogels of the present technology desirably exhibit low loss of solvent. The volatility of the compositions depends on the vapor pressure of the solvent used. In various embodiments, the organogel composition includes at least one solvent having a vapor pressure less than 24 mm Hg at room temperature. In at least one embodiment, the organogel composition includes at least one solvent having a vapor pressure of from about 0.01 mm Hg to about 23.8 mm Hg, about 0.05 mm Hg to about 20 mm Hg, about 0.1 mm Hg to about 10 mm Hg, about 0.5 mm Hg to about 5 mm Hg, or about 0.01 mm Hg to about 1.0 mm Hg, and ranges between and including any two of these values, or less than any one of these values. In at least one embodiment, the organogel composition includes at least one solvent having a vapor pressure of from about 0.01 mm Hg to about 1.0 mm Hg.

In accordance with embodiments of the present technology, the organogels suitably retain their mechanical strength during and after the graft implanting process to maintain the graft in the required position. Accordingly, the organogel has a static compressive modulus of greater than about 0.1 MPa. This includes a compressive modulus of about 0.5 MPa to about 18 MPa, about 2 MPa to about 15 MPa, about 3 MPa to about 12 MPa, about 5 MPa to about 10 MPa and values between and including any two of these values, or less than any one of these values. In at least one embodiment, the organogel has a compressive modulus of about 1 MPa to about 50 Mpa, about 5 MPa to about 40 Mpa, about 10 MPa to about 30 Mpa, about 15 MPa to about 25 Mpa, and ranges between and including any two of these values, or less than any one of these values. Static compressive modulus and dynamic compressive modulus represent the ratio of stress to strain in compression under static and vibratory conditions, respectively. In at least one embodiment, the composition has a static compressive modulus of from about 1 MPa to about 15 MPa. In at least one embodiment, the composition has an elastic modulus of from about 0.5 MPa to about 2.5 MPa. In some other embodiments, the composition has a sheer modulus of from about 0.1 MPa to about 3 MPa.

In various embodiments, the organogels of the present technology may desirably exhibit low shrinkage-swelling characteristics. For example, the volume of the organogel may shrink less than about 15%, less than about 10% or less than about 5% after curing. In various embodiments, the organogels of the present technology may exhibit improved stability as compared to other comparable compositions. For example, the moduli of organogels changed very little in accelerated aging tests conducted in accordance with the stability and/or accelerated stability tests described herein.

The compositions described herein may be generally used for implantable prostheses and particularly in or as sealing compositions for sealing endoluminal devices to vessel walls, or for filling into filling structures in lumens such as aneurysm sacs. The sealing of endoluminal devices, or the filling of aneurysm sac, facilitates retention of blood flow through the device.

In one aspect, a method of forming an organogel is provided. The method includes delivering a composition including a first part including a first solution and a second part including a second solution to the intended site of formation of the organogel; contacting the first solution with the second solution; and initiating polymerization of the pre-polymer to form an organogel. The first solution and the second solution are as described herein. In at least one embodiment of the method, the first solution may include one or more pre-polymers, a non-aqueous solvent, a polymerization co-initiator or initiator and optionally one or more chain extenders; and the second solution may include a polymerization initiator or co-initiator, a non-aqueous solvent and optionally one or more chain extenders. In at least one embodiment of the method, the first solution or the second solution, or both solutions may further include one or more additives. Suitable additives are described hereinabove and may be selected from the group consisting of fillers, contrast agents, processing aids, plasticizers, and viscosity-reducing agents. It will be understood that when the first solution includes an initiator, the second solution may include a co-initiator, and vice versa.

In one aspect, a method for using the organogel in systems for the endoluminal treatment of aneurysms is provided. In one aspect, a device including the composition described herein, or into which the composition described herein is filled, is provided. The device may be a graft system and may include a support or a scaffold. In at least one embodiment, the device includes a system for the endoluminal treatment of aneurysms, including both abdominal aortic aneurysms (AAA's) and thoracic aortic aneurysms (TAA's). The systems include prostheses which include double-walled filling structures which are pre-shaped and otherwise adapted to substantially fill the enlarged volume of an aneurysm when filled, leaving a lumen in place for blood flow. In various embodiments, the systems may include prostheses which include double-walled filling structures which are pre-shaped and otherwise adapted to sufficiently fill the enlarged volume of an aneurysm when filled, leaving a lumen in place for blood flow. In some embodiments, sufficiently filled may include enough fill to, e.g. avoid migration, support lumen, etc. An example of such systems and methods is described in U.S. Pat. No. 8,048,145, the full disclosure of which is incorporated herein by reference.

In one aspect, the present technology provides methods and systems for the endoluminal treatment of aneurysms, particularly aortic aneurysms including both abdominal aortic aneurysms (AAA's) and thoracic aortic aneurysms (TAA's). The systems include prostheses which comprise double-walled filling structures which are pre-shaped and otherwise adapted to substantially fill or sufficiently fill the enlarged volume of an aneurysm when filled, particularly a fusiform aneurysm, leaving a lumen in place for blood flow.

An exemplary single prosthesis system comprising a filling structure mounted over a delivery catheter is illustrated in FIG. 1. A system 10 constructed for delivering a double-walled filling structure 12 to an aneurysm includes the filling structure 12 and a delivery catheter 14 having an expandable element 16, typically an inflatable balloon, at its distal end. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure 12. Upon inflation with the filling material or medium, the outer wall 24 will expand radially outwardly, as shown in broken line, as will the inner wall 26, also shown in broken line. Expansion of the inner wall 26 defines an internal lumen 28. The expandable element 16, such as a balloon or other structure, is expandable to support an inner surface of the lumen 28, as also shown in broken line in FIG. 1.

Figure 2:
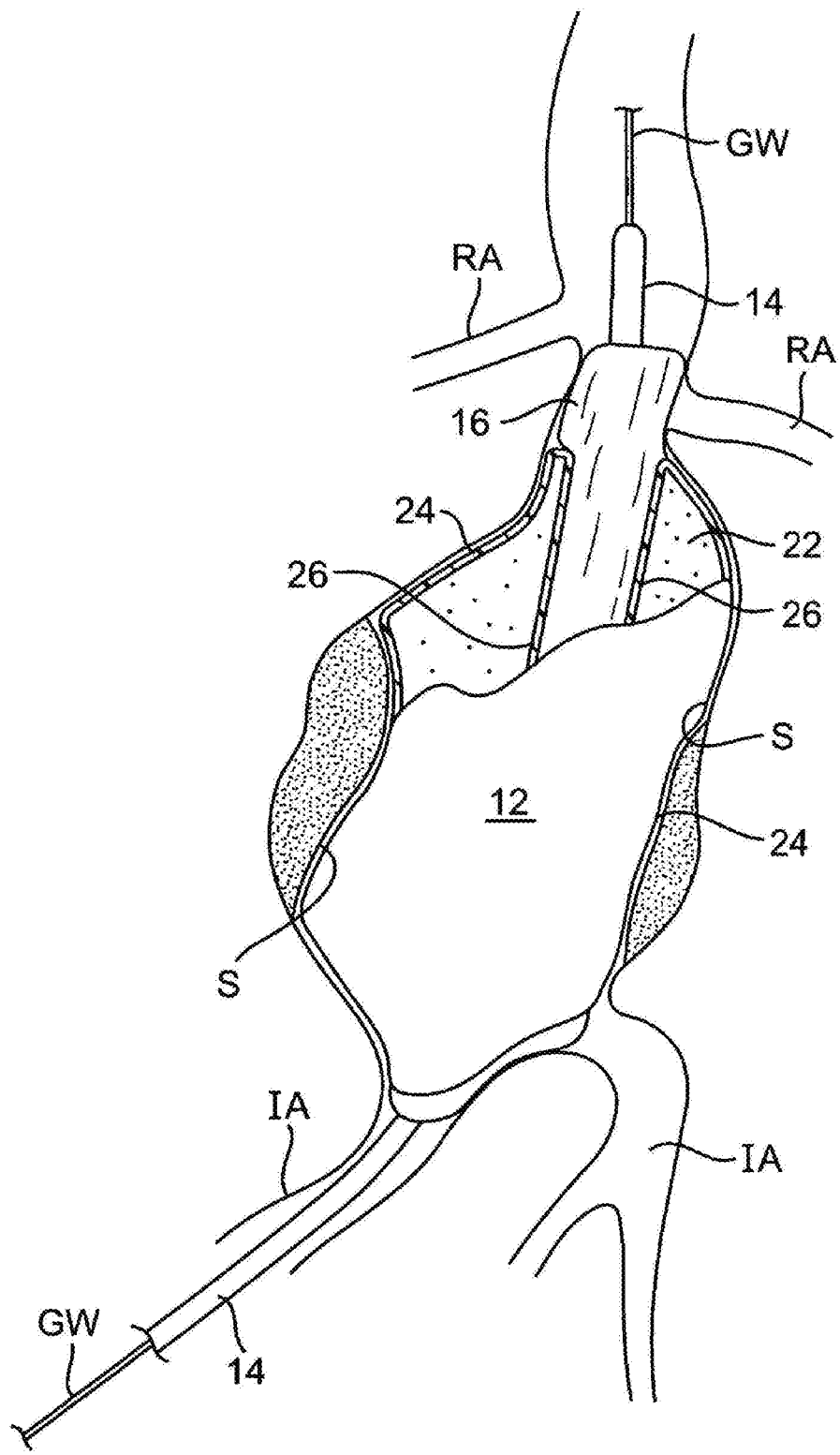
FIG. 2 illustrates use of an embodiment of the prosthesis system of FIG. 1 for treating an infrarenal abdominal aortic aneurysm.

The treatment system 10 of FIG. 1 may be utilized as shown in FIG. 2 to treat the complex geometry of a transmural abdominal aortic aneurysm (AAA) by first positioning the delivery catheter 14 to place the double-walled filling structure 12 (in its unfilled configuration) generally across the aneurysm from the region of the aorta beneath the renal arteries (RA) to a region over the iliac arteries (IA). Usually, the delivery catheter 14 will be introduced over a guidewire (GW) through a puncture in the patient's groin accessing the iliac artery by the Seldinger technique. After the double-walled filling structure 12 is properly positioned, precursor for forming an organogel of the present technology is introduced into the internal space 22. Filling the internal space 22 expands the outer wall 24 of the structure outwardly so that it conforms to the inner surface (S) of the aneurismal space. Before, during, or after filling of the double-walled filling structure 12 with inflation medium, the expandable element 16, such as a balloon or other expansible structure, will also be inflated or expanded to open the tubular lumen defined by the interior of the inner wall 26.

Figure 3:
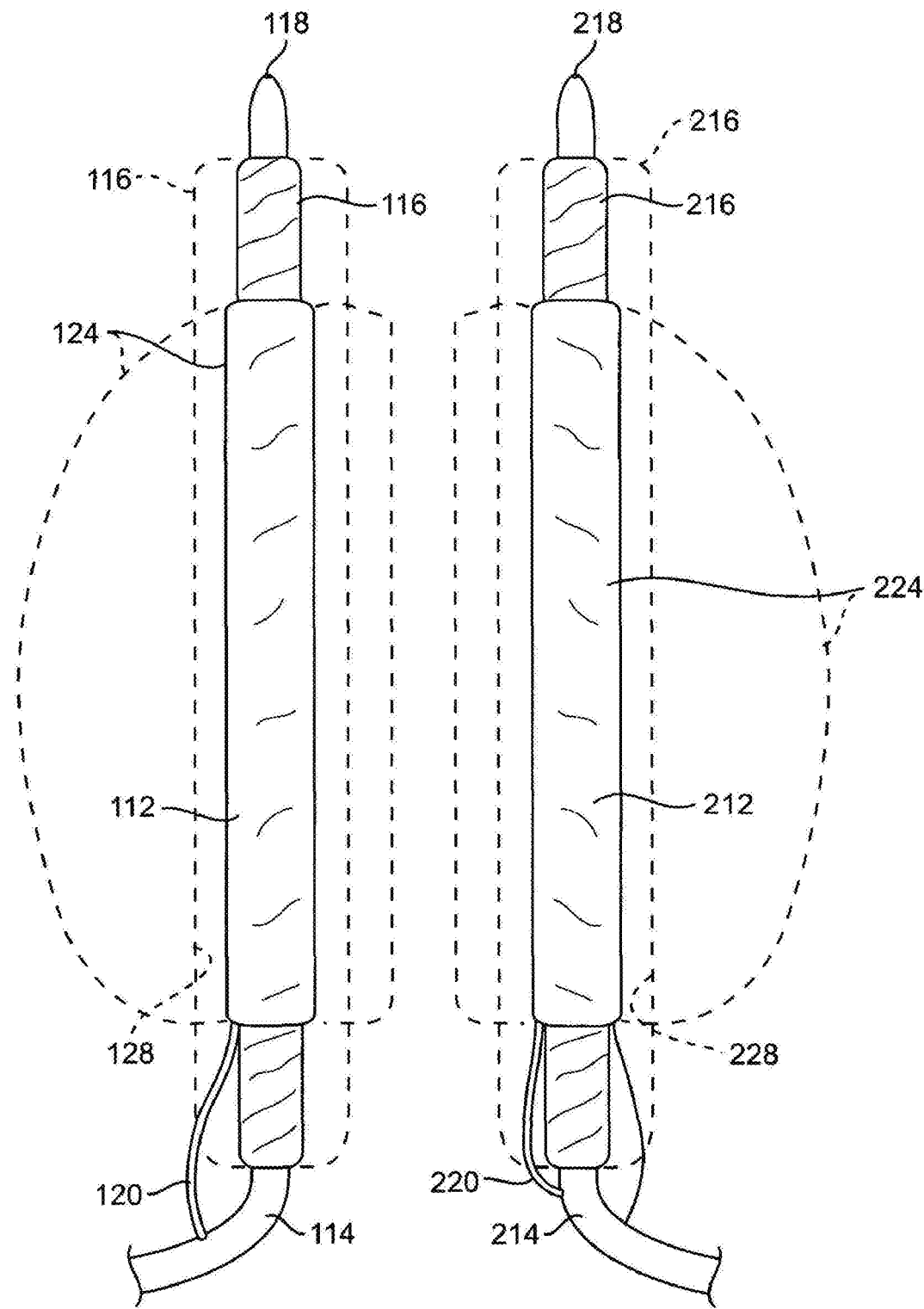
FIG. 3 illustrates a system comprising a pair of prostheses for delivery to an infrarenal abdominal aortic aneurysm, where each prosthesis comprises a filling structure mounted on a delivery catheter, and fillable with a composition of the present technology.

In at least one embodiment, a pair of double-walled filling structures can be used to treat infrarenal abdominal aortic aneurysms, instead of only a single filling structure as illustrated in FIG. 2. A system comprising such a pair of filling structures is illustrated in FIG. 3 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1, and corresponding parts of each of the fillings systems 112 and 212 will be given identical numbers with either the 100 base number or 200 base number. As shown in FIG. 3, the delivery catheter 114 includes a guidewire lumen 118 and a filling tube 120. The delivery catheter 214 includes a guidewire lumen 218 and a filling tube 220. The first filling structure 112 includes an outer wall 124. The second filling structure 212 includes an outer wall 224. The outer wall 124 and the outer wall 224 are expandable to allow for filling of the first filling structure 112 and the second filling structure 212, respectively, as shown by the broken lines. An expandable element 116, such as a balloon or other structure, is expandable to support an inner surface of a lumen 128, as shown in broken line in FIG. 3, and an expandable element 216, such as a balloon or other structure, is expandable to support an inner surface of a lumen 228, as also shown in broken line in FIG. 3.

A principal difference between the filling structures 112 and 212 in FIG. 3, on the one hand, and the filling structure 12 of FIG. 1 is that the pair of filling structures will generally have asymmetric configurations which are meant to be positioned adjacent to each other within the aneurismal space and to in combination fill that space. After filling the filling structures 112 and 212 of FIG. 3 with any of the two-part compositions of the present technology, the composition will be cured or otherwise hardened to form the organogels of the present technology, and the delivery catheters 114 and 214 removed, respectively. The hardened filling structures will then provide a pair of tubular lumens opening from the aorta beneath the renal arteries to the right and left iliac arteries. The ability of the filling structures 112 and 212 to conform to the inner surface of the aneurysm helps the structures to remain immobilized within the aneurysm with little or no migration.

In addition to the filling structures described hereinabove, the systems may further include at least a first scaffold separate from the filling structure, where the scaffold can be expanded within the generally tubular lumen which provides the blood flow after the filling structure has been deployed in the aneurysm. The first scaffold will be adapted to expand within at least a first portion of the tubular lumen of the filling structure and may provide one or more specific advantages. For example, the scaffold may support and smooth the inside wall of the tubular lumen which in some cases might otherwise become uneven during hardening of the polymer fill. Scaffolds may also provide for anchoring of the filling structure, particularly at the aortic end of the graft when placed in an AAA. The scaffold may be partly or wholly covered with a membrane in order to form a graft. In such cases, the graft structure may help provide a transition from the blood vessel into the generally tubular lumen of the filling structure from the aortic end. Alternatively, the graft structure could provide one or a pair of transitions out of the iliac end of the filling structure. In a particular example, a graft structure can be used on either side of the filling structure in order to treat additional or continuing aneurysmal regions in the adjacent blood vessel. In at least one embodiment, the system may include multiple scaffold structures. For example, the system may include at least a first and a second scaffold, one for each of the tubular lumens defined by the first and second double-walled filling structures, respectively. The scaffolds may be adapted to be placed in series, frequently overlapping, or may be adapted to be spaced apart at either or both ends and optionally at regions between the ends.

Figure 4:
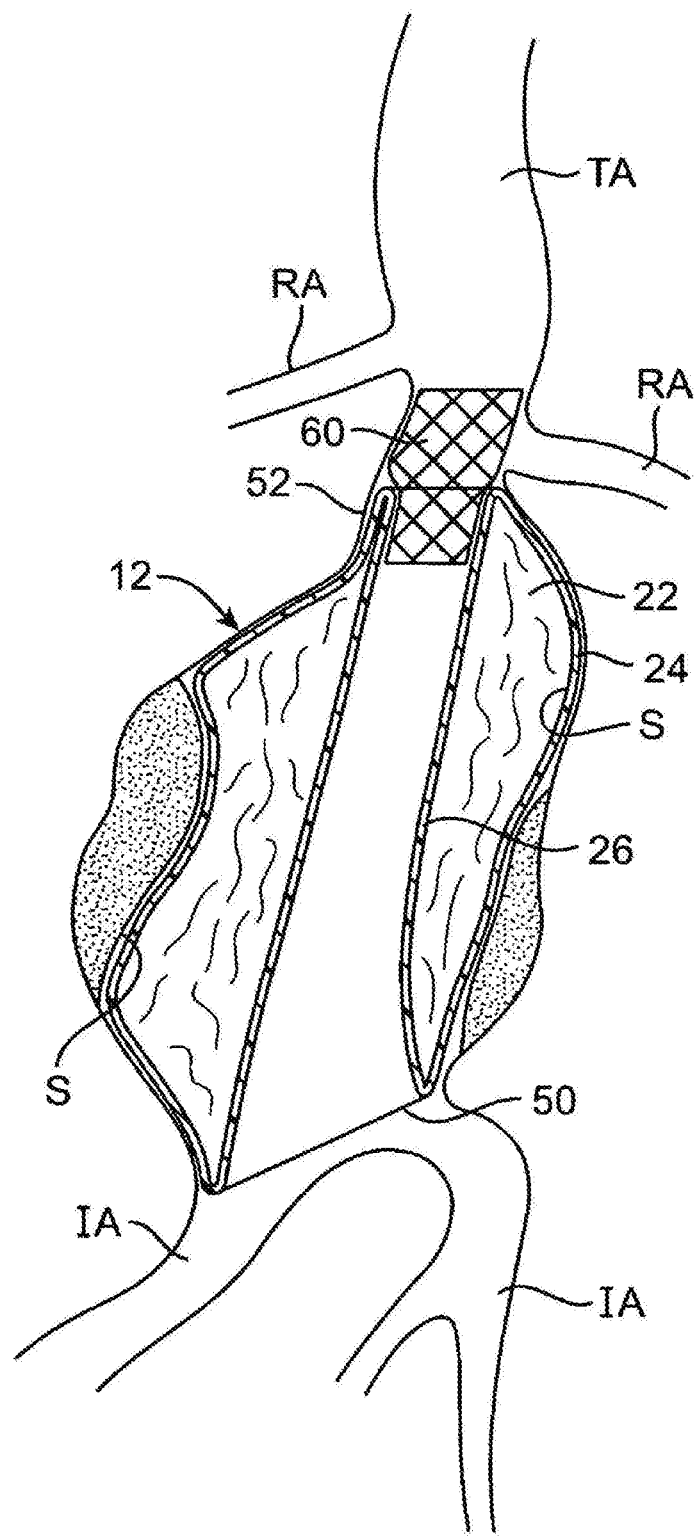
FIG. 4 illustrates use of an embodiment of the prosthesis system of FIG. 1 for treating an infrarenal abdominal aortic aneurysm.

An example of a short, stent-like scaffold structure for a single prosthesis system is illustrated in FIG. 4. A scaffold 60 may be implanted in an upper opening 52 of a tubular lumen of the filling structure 12 in order to help anchor an upper end of the filling structure 12 and prevent intrusion of blood into a region between the outer wall 24 and the inner surface (S) of the aneurysm and to generally improve a transition from the aorta into the tubular lumen. Locations of the renal arteries (RA) and iliac arteries (IA) with regard to the thoracic aorta (TA) and with respect to a position of the filling structure 12 are shown in FIG. 4 for an embodiment. The filling structure 12 includes the outer wall 24 and the inner wall 26 that define the internal space 22 therebetween. The tubular lumen of the filling structure 12 also has a lower end 50.

A stent-like structure for the filling structure 12 or other stent graft usable to treat an aneurysm may include any conventional stent, graft, or other expandable luminal support structure known in the art. For example, a graft may include one or more circumferential inflatable channels extending around the entire circumference of the graft body or may extend partially around the circumference of the graft body. The circumferential inflatable channels may be in communication with each other via a longitudinal inflatable fill channel. The network of inflatable channels may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the graft body by virtue of the mechanical properties of the hardened material disposed within the channels. An example of such systems and methods is described in U.S. Patent Publication No. 2014/0100650, the full disclosure of which is incorporated herein by reference. In at least one embodiment, the inflatable channels may be filled with the organogel compositions of the present technology.

The present technology, thus generally described, will be understood more readily by reference to the following Examples, which are provided by way of illustration and are not intended to be limiting of the present technology.

EXAMPLES

The following Examples are illustrative only and are not intended to limit the scope of other embodiments described in any way.

The following abbreviations are used in all examples:
ATU: 1-acetyl-2-thiourea
BPO: benzoyl peroxide
CHP: cumene hydroperoxide
DHEPT: N, N-dihydroxyethyl-p-toluidine
PTU: 1-(2-pyridyl)-2-thiourea
PEG-T: Ethoxylated (20) Trimethylolpropane Triacrylate
PEGDMA 1000: Poly(ethylene glycol) dimethacrylate MW 1000
PEGDMA 8000: Poly(ethylene glycol) dimethacrylate MW 8000
PEGDMA 10,000: Poly(ethylene glycol) dimethacrylate MW 10,000
PEGMEMA 950: Poly(ethylene glycol) methylether methacrylate MW 950
PEGMEMA 500: Poly(ethylene glycol) methylether methacrylate MW 500
PEGMEMA 300: Poly(ethylene glycol) methylether methacrylate MW 300
PEGMMA 2000: Poly(ethylene glycol) mono methacrylate MW 2000
PG: Propylene Glycol
DPG: Dipropylene Glycol
TPG: Tripropylene Glycol
TPGME: Tripropylene Glycol methyl ether
DEGEE: di(ethylene glycol) ethyl ether
DPGBE: di(propylene glycol) butyl ether
BC: Butylene Carbonate
DMTDP: dimethyl 3,3'-thiodipropionate
NaDi: Sodium diatrizoate hydrate
PPGDA 2000: Poly(propylene glycol) diacrylate MW 2000
PPGDMA 2000: Poly(propylene glycol) dimethacrylate MW 2000
H Q Hydroquinone
MEHQ Methyl ether hydroquinone
BHT Butylated hydroxytoluene
DMSO Dimethyl sulfoxide Example 1: Preparation of Organogels The organogels were prepared by mixing together two solutions, namely C1 and C2. First, the C1 and C2 solutions were prepared separately by mixing together appropriate ingredients in suitable amounts until the solutions are homogenous and any solid matter that is part of the formulation is completely dissolved. Then C1 was added to C2 (or C2 was added to C1) and the two components are mixing together for 5 to 15 second under constant agitation. Alternatively, two barrel cartridges, barrel 1 and barrel 2, were filled with C1 and C2, respectively, and the solutions were mixed together during dispensing of the solution though a static mixer into an appropriate container. The final mixed solution was placed in a 37° C. water bath and monitored until the gelation was completed. An illustration of formation of the organogel composition is depicted in FIG. 6.

| Composition 1 | | |
|---|---|---|
| | wt. % | |
| Raw Material | C1 | C2 |
| PEG-T | 29.56 | — |
| PG | 19.70 | 49.08 |
| PTU | 0.74 | — |
| CHP @ 80%* | — | 0.92 |
| Combined formulation | | 100% |

*CHP is supplied at 80% with the other 20% being an aromatic solvent.

Additional organogels are prepared using the methods described above.

| Composition 2 | | |
|---|---|---|
| | wt. % | |
| Raw Material | C1 | C2 |
| PEG-T | 24.61 | — |
| PEGDMA 1000 | 6.00 | — |
| PG | 18.62 | 49.04 |
| PTU | 0.77 | — |
| CHP @ 80% | — | 0.96 |
| Combined formulation | | 100% |

| Composition 3 | | |
|---|---|---|
| | wt. % | |
| Raw Material | C1 | C2 |
| PEG-T | 24.53 | — |
| PEGMEMA 950 | 11.48 | — |
| PG | 13.06 | 48.84 |
| PTU | 0.93 | — |
| CHP @ 80% | — | 1.16 |
| Combined formulation | | 100% |

| Composition 4 | | |
|---|---|---|
| | wt. % | |
| Raw Material | C1 | C2 |
| PEG-T | 19.74 | — |
| PEGMEMA 500 | 5.92 | — |
| PG | 23.7 | 49.20 |
| PTU | 0.64 | — |
| CHP @ 80% | — | 0.80 |
| Combined formulation | | 100% |

| Composition 5 | | |
|---|---|---|
| | wt. % | |
| Raw Material | C1 | C2 |
| PEG-T | 19.69 | — |
| PEGMEMA 950 | 11.51 | — |
| PG | 18.01 | 49.01 |
| PTU | 0.79 | — |
| CHP @ 80% | — | 0.99 |
| Combined formulation | | 100% |

| Composition 6 | | |
|---|---|---|
| | wt. % | |
| Raw Material | C1 | C2 |
| PEG-T | 24.53 | — |
| PEGMEMA 950 | 11.48 | — |
| PG | 13.06 | 48.84 |
| PTU | 0.93 | — |
| CHP @ 80% | — | 1.16 |
| Combined formulation | | 100% |

| Composition 7 | | |
|---|---|---|
| | wt. % | |
| Raw Material | C1 | C2 |
| PEG-T | 29.56 | — |
| DEGEE | 19.70 | 49.08 |
| PTU | 0.74 | — |
| CHP @ 80% | — | 0.92 |
| Combined formulation | | 100% |

| Composition 8 | | |
|---|---|---|
| | wt. % | |
| Raw Material | C1 | C2 |
| PEG-T | 29.56 | — |
| DPGBE | 19.70 | 49.08 |
| PTU | 0.74 | — |
| CHP @ 80% | — | 0.92 |
| Combined formulation | | 100% |

| Composition 9 | | |
|---|---|---|
| | wt. % | |
| Raw Material | C1 | C2 |
| PEG-T | 29.56 | — |
| BC | 19.70 | 49.08 |
| PTU | 0.74 | — |
| CHP @ 80% | — | 0.92 |
| Combined formulation | | 100% |

Composition 10

| Raw Material | C1 | C2 |
| --- | --- | --- |
| PEG-T | 29.56 | — |
| PG | 19.70 | 49.08 |
| ATU | 0.74 | — |
| CHP @ 80% | — | 0.92 |
| Combined formulation | | 100% |

Composition 11

| Raw Material | C1 | C2 |
| --- | --- | --- |
| PEG-T | 24.54 | — |
| PPGDA 2000 | 12.07 | — |
| TPG | 12.47 | 48.85 |
| PTU | 0.92 | — |
| CHP @ 80% | — | 1.15 |
| Combined formulation | | 100% |

Composition 12

| Raw Material | C1 | C2 |
| --- | --- | --- |
| PEG-T | 12.81 | — |
| PPGDMA 2000 | 17.04 | — |
| TPG | 19.41 | 49.08 |
| PTU | 0.74 | — |
| CHP @ 80% | — | 0.92 |
| Combined formulation | | 100% |

Composition 13

| Raw Material | C1 | C2 |
| --- | --- | --- |
| PEG-T | 14.32 | — |
| PEGMMA 2000 | 7.42 | — |
| TPG | 27.70 | 49.30 |
| PTU | 0.56 | — |
| CHP @ 80% | — | 0.70 |
| Combined formulation | | 100% |

Composition 14

| Raw Material | C1 | C2 |
| --- | --- | --- |
| PEG-T | 29.59 | — |
| DEGEE | 19.76 | 49.26 |
| DHEPT | 0.74 | — |
| Benzoyl Peroxide | — | 0.74 |
| Combined formulation | | 100% |

Composition 15

| Raw Material | C1 | C2 |
| --- | --- | --- |
| PEG-T | 29.59 | — |
| TPGME | 19.67 | 49.08 |
| PTU | 0.74 | — |
| CHP @ 80% | — | 0.92 |
| Combined formulation | | 100% |

Composition 16

| Raw Material | C1 | C2 |
| --- | --- | --- |
| PEG-T | 29.44 | — |
| PG | 19.59 | 49.08 |
| DMTDP | 0.23 | — |
| PTU | 0.74 | — |
| CHP @80% | — | 0.92 |
| Combined formulation | | 100% |

Composition 17

| Raw Material | C1 | C2 |
| --- | --- | --- |
| PEG-T | 29.59 | — |
| PG | | 49.08 |
| Nonanol | 19.67 | — |
| PTU | 0.74 | — |
| CHP @80% | — | 0.92 |
| Combined formulation | | 100% |

Composition 18

| Raw Material | C1 | C2 |
| --- | --- | --- |
| PEG-T | 28.20 | — |
| PG | 21.10 | 44.7 |
| NaDi | — | 4.42 |
| PTU | 0.70 | — |
| CHP @80% | — | 0.88 |
| Combined formulation | | 100% |

Composition 19

| Raw Material | C1 | C2 |
| --- | --- | --- |
| PEG-T | 25.00 | — |
| PEGDMA 8000 | | 12.00 |
| BC | 24.38 | 37.22 |
| PTU | 0.62 | — |
| CHP @80% | — | 0.78 |
| Combined formulation | | 100% |

| Composition 20 | | |
|---|---|---|
| | wt. % | |
| Raw Material | C1 | C2 |
| PEG-T | 25.00 | — |
| PEGDMA 8000 | — | 8.00 |
| BC | 18.17 | 30.76 |
| DPGBE | 6.06 | 10.25 |
| PTU | 0.77 | — |
| CHP @80% | — | 0.99 |
| Combined formulation | | 100% |

| Composition 21 | | |
|---|---|---|
| | wt. % | |
| Raw Material | C1 | C2 |
| PEG-T | 25.00 | — |
| PEGDMA 10,000 | — | 12.00 |
| BC | 24.37 | 37.09 |
| PTU | 0.63 | — |
| CHP @80% | — | 0.91 |
| Combined formulation | | 100% |

| Composition 22 | | |
|---|---|---|
| | wt. % | |
| Raw Materials | C1 | C2 |
| PEG-T | 29.59 | |
| PG | 19.67 | 49.065 |
| HQ | | 0.015 |
| CHP @80% | | 0.92 |
| PTU | 0.74 | |
| Combined formulation | | 100% |

| Composition 23 | | |
|---|---|---|
| | wt. % | |
| Raw Materials | C1 | C2 |
| PEG-T | 29.59 | |
| DPGBE | 19.67 | 49.065 |
| MEHQ | | 0.015 |
| CHP @80% | | 0.92 |
| PTU | 0.74 | |
| Combined formulation | | 100% |

| Composition 24 | | |
|---|---|---|
| | wt. % | |
| Raw Materials | C1 | C2 |
| PEG-T | 24.52 | |
| PG | | 39.25 |
| DMSO | 24.52 | |
| PEGDMA 1000 | | 9.80 |
| CHP @80% | 1.06 | |
| PTU | | 0.85 |
| Combined formulation | | 100% |

| Composition 25 | | |
|---|---|---|
| | wt. % | |
| Raw Materials | C1 | C2 |
| PEG-T | 24.508 | |
| PG | | 39.25 |
| DMSO | 24.52 | |
| PEGDMA 1000 | | 9.80 |
| CHP @80% | 1.06 | |
| PTU | | 0.85 |
| BHT | 0.012 | |
| Combined formulation | | 100% |

| Composition 26 | | |
|---|---|---|
| | wt. % | |
| Raw Materials | C1 | C2 |
| PEG-T | 24.06 | |
| PG | 28.86 | |
| DMSO | | 19.24 |
| PEGMEMA 500 | | 24.06 |
| CHP @80% | | 1.02 |
| PTU | 0.82 | |
| BHT | 0.011 | |
| NaDi | | 1.92 |
| Combined formulation | | 100% |

| Composition 27 | | |
|---|---|---|
| | wt. % | |
| Raw Materials | C1 | C2 |
| PEG-T | | 25.28 |
| PG | | 34.11 |
| DMSO | 21.75 | |
| PEGMEMA 500 | 8.43 | |
| PEGMEMA 950 | 8.43 | |
| CHP @80% | 0.65 | |
| PTU | | 0.52 |
| NaDi | 0.83 | |
| Combined formulation | | 100% |

| Composition 28 | | |
|---|---|---|
| | wt. % | |
| Raw Materials | C1 | C2 |
| PEG-T | | 18.58 |
| PG | | 29.34 |
| DMSO | 19.56 | |
| PEGMEMA 500 | 13.20 | |
| PEGMEMA 950 | 13.20 | |
| PEGDMA 1000 | 2.93 | |
| CHP @80% | 0.77 | |
| PTU | | 0.61 |
| BHT | | 0.98 |
| NaDi | 0.83 | |
| Combined formulation | | 100% |

| Composition 29 | | |
|---|---|---|
| | wt. % | |
| Raw Materials | C1 | C2 |
| PEG-T | 26.36 | |
| PG | | 29.30 |
| DMSO | 19.53 | |
| PEGMEMA 300 | 2.93 | |
| PEGDMA 1000 | | 19.53 |
| CHP @80% | 0.75 | |
| PTU | | 0.61 |
| BHT | 0.01 | |
| NaDi | | 0.49 |
| Combined formulation | 100% | |

Example 2: Characterization of Organogels

Compressive modulus for the prepared organogels was measured by single column materials testing system (Instron model number 3343) using ASTM Standard D575-91 Standard Test Method for Rubber in Compression, which is incorporated herein by reference.

Table 1 summarizes the gel set times and compressive modulus for the prepared organogels.

TABLE 1

| Composition # | Gel set time (min:sec) | Compressive Modulus (MPa) |
|---|---|---|
| 1 | 1:09 | 4.6 |
| 2 | 1:30 | 8.9 |
| 3 | 1:30 | 3.48 |
| 4 | 1:40 | 2.07 |
| 5 | — | 1.77 |
| 6 | 1:40 | 2.53 |
| 7 | 1:10 | 3.89 |
| 8 | 2:31 | 5.40 |
| 9 | 3:25 | — |
| 10 | >8:00 | 6.9 |
| 11 | — | 0.67 |
| 12 | 4:00 | 1.22 |
| 13 | <6:00 | 0.46 |
| 14 | 1:20 | 4.49 |
| 15 | 4:00 | 5.48 |
| 16 | — | 4.48 |
| 17 | 1:45 | 3.96 |
| 18 | 1:11 | 4.08 |
| 19 | 1:30 | 8.5 |
| 20 | — | 5.4 |
| 21 | — | 3.7 |
| 22 | 1:54 | 7.01 |
| 23 | 2:10 | 4.44 |
| 24 | 2:05 | 6.48 |
| 25 | 2:00 | 6.65 |
| 26 | 2:15 | 6.30 |
| 27 | 3:00 | 3.93 |
| 28 | 3:30 | 5.95 |
| 29 | 2'00" | 9.52 |

Example 3: Stability Testing

The organogels prepared above were screened for shelf life stability of the individual polymer system components (C1 and C2 solutions) under accelerated conditions at 60° C. for an equivalent time corresponding to 18 months at room temperature. The results showed the individual component solutions were stable and once combined formed organogels suitable for intended application.

The organogel of composition 1 was tested in conjunction with an endobag (Endologix) as a component of an endovascular aneurysm repair system in which the endobag surrounds a stent placed in an abdominal aortic aneurysm (AAA). The endobag was pre-filled and flushed with saline to remove air and determine the fill volume. Following flushing, the two-component polymer system from Composition 1 was injected into the endobag using a 2-barrel cartridge dispensed using a ratcheted gun at 180 mm Hg pressure. The endobag maintained its pre-set shape thereby illustrating the stability of the organogel.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

What is claimed is:

1. An organogel composition comprising two parts, a first part comprising a first solution and a second part comprising a second solution, wherein
    the first solution comprises one or more pre-polymers, a non-aqueous solvent, a polymerization co-initiator or initiator, and optionally one or more chain extenders and additives; and
    the second solution comprises a polymerization initiator or co-initiator, a non-aqueous solvent, and optionally one or more chain extenders and additives,
    wherein the first part and the second part are separate from each other,
    wherein the non-aqueous solvent of the first solution does not react with the one or more pre-polymers in the first solution,
    wherein the one or more pre-polymers comprises compounds having at least two functional groups selected from acrylate, methacrylate, and vinyl functional groups, the one or more pre-polymers selected from the group consisting of ethoxylated (3) bisphenol A diacrylate, ethoxylated (30) bisphenol A diacrylate (EBPADA), ethoxylated (9) trimethylolpropane triacrylate, ethoxylated (15) trimethylolpropane triacrylate, ethoxylated (20) trimethylolpropane triacrylate (PEG-T), propoxylated (3) trimethylolpropane triacrylate (PTMPTA), pentaerythritol triacrylate, ethoxylated (4) pentaerythritol tetraacrylate, pentaerythritol tetraacrylate, the methacrylic variants of the aforesaid acrylates, divinyl adipate, 1,4-dibutane diol divinyl ether, di and tri-ethylene glycol divinyl ether, allyl ether, diallyl maleate, trimethyl propane diallyl ether, and combinations thereof, and
    wherein a combination of the first part and second part
        exhibits a viscosity of from about 5 cP to about 100 cP, at 25° C., 30% solution, and
        forms an organogel exhibiting a static compressive modulus of from about 0.1 MPa to about 50 MPa, measured in accordance with ASTM D575-91, within a gel time of about 30 seconds to about 30 minutes.

2. The organogel composition of claim 1, wherein the non-aqueous solvent comprises aliphatic and/or aromatic solvents selected from the group consisting of alcohols, aldehydes, amides, carbonates, ethers, esters, glycols, glycol ethers, glycol esters, hydrocarbons, ketones, sulfoxides, and vegetable oils.

3. The organogel composition of claim 2, wherein the non-aqueous solvent is selected from the group consisting of methanol, glycerin, ethylene glycol, propylene glycol, butylene glycol, dipropylene glycol, diethylene glycol, tripropylene glycol, polyethylene glycol, ethyl ether, tripropylene glycol methyl ether, di(propylene glycol) butyl ether, propylene carbonate, butylene carbonate, benzene, toluene, xylene, methyl ethyl ketone, castor oil, linseed oil, sesame oil, soybean oil, olive oil, and combinations thereof.

4. The organogel composition of claim 1, wherein the chain extender comprises mono-- or di-functional compounds having acrylate, methacrylate or vinyl functional groups.

5. The organogel composition of claim 4, wherein the chain extender is selected from the group consisting of polyethylene glycol monoacrylate (PEGMA), polypropylene glycol monoacrylate (PPGMA), polyethylene glycol diacrylate (PEGDA), polypropylene glycol diacrylate (PPGDA), dipropylene glycol diacrylate (DPGDA), tetraethylene glycol diacrylate (TEGDA), tripropylene glycol diacrylate (TPGDA), polyethylene glycol mono methacrylate (PEGMMA), polypropylene glycol mono methacrylate (PPGMMA), polyethylene glycol methyl ether methacrylate (PEGMEMA), polyethylene glycol dimethacrylate (PEGDMA), polypropylene glycol dimethacrylate (PPGDMA), and combinations thereof.

6. The organogel composition of claim 1, wherein the polymerization initiator comprises peroxides and hydroperoxides.

7. The organogel composition of claim 6, wherein the polymerization initiator is selected from the group consisting of benzoyl peroxide (BPO), cumene hydroperoxide (CHP), Di-cumyl peroxide (CPO), lauryl peroxide, tert-amyl hydroperoxide (t-AHP), tert-butyl hydroperoxide (t-BHP), di-tert-butyl peroxide (DTBP), tributyl hydroperoxide (TBPH), tetra-methyl butyl hydroperoxide (MBHP), and combinations thereof.

8. The organogel composition of claim 1, wherein the polymerization co-initiator is selected from the group consisting of tri-ethanol amine (TEA), 1-(2-pyridyl)-2-thiourea (PTU), 1-acetyl-2-thiourea (ATU), N, N-dihydroxyethyl-p-toluidine (DHEPT), 4-(di-methyl amino) phenethyl alcohol (DMAPE), ethyl 4-(dimethylamino)benzoate (EDMAB), 2-[4-(dimethylamino)phenyl]ethanol, N,N-dimethyl-p-toluidine (DMPT), bis(hydroxyethyl)-p-toluidine, and combinations thereof.

9. The organogel composition of claim 1, wherein either or both of the first and second solutions further comprise a co-solvent.

10. The organogel composition of claim 9, wherein the co-solvent is selected from the group consisting of nonanol, dimethyl sulfoxide, butylene carbonate, di-ethylene glycol ethyl ether, di-propylene glycol methyl ether, di-propylene glycol butyl ether, tri-propylene glycol methyl ether and tri-propylene glycol butyl ether, and combinations thereof.

11. The organogel composition of claim 1, further comprising one or more additives.

12. The organogel composition of claim 11, wherein the one or more additives are selected from the group consisting of fillers, contrast agents, processing aids, plasticizers, and viscosity-reducing agents.

13. An organogel comprising the composition of claim 1, wherein the organogel is formed from the combination of the first part and the second part.

14. The organogel of claim 13, wherein the organogel exhibits a static compressive modulus of from about 1 MPa to about 18 MPa, measured in accordance with ASTM D575-91.

15. The organogel of claim 13, wherein the organogel exhibits a gel time of about 1 min to about 20 min.

16. The organogel composition of claim 1, further comprising a total composition weight, wherein the non-aqueous solvent in the first part is present in an amount greater than 50% by weight of the total composition weight.

17. A system for treating an aneurysm, the system comprising a filling structure filled with the organogel composition according to claim 1.

18. An organogel composition comprising two parts, a first part comprising a first solution and a second part comprising a second solution, wherein
the first solution comprises one or more pre-polymers, a non-aqueous solvent, a polymerization co-initiator or initiator, and optionally one or more chain extenders and additives; and
the second solution comprises a polymerization initiator or co-initiator, a non-aqueous solvent, and optionally one or more chain extenders and additives,
wherein the first part and the second part are separate from each other,
wherein the non-aqueous solvent of the first solution does not react with the one or more pre-polymers in the first solution,
wherein the one or more pre-polymers comprises compounds having at least two functional groups selected from acrylate, methacrylate, and vinyl functional groups, the one or more pre-polymers selected from the group consisting of ethoxylated (3) bisphenol A diacrylate, ethoxylated (30) bisphenol A diacrylate (EBPADA), ethoxylated (9) trimethylolpropane triacrylate, ethoxylated (15) trimethylolpropane triacrylate, ethoxylated (20) trimethylolpropane triacrylate (PEG-T), propoxylated (3) trimethylolpropane triacrylate (PTMPTA), pentaerythritol triacrylate, ethoxylated (4) pentaerythritol tetraacrylate, pentaerythritol tetraacrylate, the methacrylic variants of the aforesaid acrylates, divinyl adipate, 1,4-dibutane diol divinyl ether, di and tri-ethylene glycol divinyl ether, allyl ether, diallyl maleate, trimethyl propane diallyl ether, and combinations thereof,
wherein the non-aqueous solvent includes aliphatic and/or aromatic solvents, the non-aqueous solvent selected from the group consisting of alcohols, aldehydes, amides, carbonates, ethers, esters, glycols, glycol ethers, glycol esters, hydrocarbons, ketones, sulfoxides, and vegetable oils, and
wherein a combination of the first part and second part forms an organogel exhibiting a static compressive modulus of from about 0.1 MPa to about 50 MPa, measured in accordance with ASTM D575-91, within a gel time of about 30 seconds to about 30 minutes.

19. A system for treating an aneurysm, the system comprising a filling structure filled with the organogel composition according to claim 18.

20. A method of forming an organogel comprising:
contacting a first part of a composition and a second part of the composition, wherein
the first part of the composition comprises a first solution comprising one or more pre-polymers, a non-aqueous solvent, a polymerization co-initiator or initiator, and optionally one or more chain extenders and additives; and
the second part of the composition comprises a second solution comprising a polymerization initiator or co-initiator, a non-aqueous solvent, and optionally one or more chain extenders and additives,
wherein the first part and second part are separate from each other prior to contacting,
wherein the non-aqueous solvent of the first solution does not react with the one or more prepolymers in the first solution,
wherein the one or more pre-polymers comprises compounds having at least two functional groups selected from acrylate, methacrylate, and vinyl functional groups, the one or more pre-polymers selected from the group consisting of ethoxylated (3) bisphenol A diacrylate, ethoxylated (30) bisphenol A diacrylate (EBPADA), ethoxylated (9) trimethylolpropane triacrylate, ethoxylated (15) trimethylolpropane triacrylate, ethoxylated (20) trimethylolpropane triacrylate (PEG-T), propoxylated (3) trimethylolpropane triacrylate (PTMPTA), pentaerythritol triacrylate, ethoxylated (4) pentaerythritol tetraacrylate, pentaerythritol tetraacrylate, the methacrylic variants of the aforesaid acrylates, divinyl adipate, 1,4-dibutane diol divinyl ether, di and tri-ethylene glycol divinyl ether, allyl ether, diallyl maleate, trimethyl propane diallyl ether, and combinations thereof; and
initiating polymerization of the one or more pre-polymers to form the composition exhibiting a viscosity of from about 5 cP to about 100 cP, at 25° C., 30% solution, wherein the composition forms an organogel exhibiting a static compressive modulus of from about 0.1 MPa to about 50 MPa, measured in accordance with ASTM D575-91, within a gel time of about 30 seconds to about 30 minutes.

21. The method of claim 20, wherein the one or more additives are selected from the group consisting of fillers, contrast agents, processing aids, plasticizers, and viscosity-reducing agents.

* * * * *